United States Patent [19]

Anderson

[11] Patent Number: 4,896,768

[45] Date of Patent: Jan. 30, 1990

[54] ANTI-BACTERIAL AND ANTI-VIRAL PRESATURATED WIPE PRODUCT

[75] Inventor: Leslie B. Anderson, Easton, Pa.

[73] Assignee: Lab Products, Inc., Maywood, N.J.

[21] Appl. No.: 916,074

[22] Filed: Oct. 6, 1986

[51] Int. Cl.⁴ .................. B65D 81/24; B65B 55/02
[52] U.S. Cl. ............................ 206/210; 53/425;
53/438; 53/484; 422/22
[58] Field of Search ............ 206/484, 460, 484.1,
206/484.2, 812, 438, 439, 440, 229, 210; 422/22;
53/425, 428

[56] References Cited

U.S. PATENT DOCUMENTS

| | | | |
|---|---|---|---|
| 3,057,467 | 10/1962 | Williams | 206/361 |
| 3,240,326 | 3/1966 | Miller | 206/812 X |
| 3,419,137 | 12/1968 | Walck, III | 206/484 X |
| 3,439,469 | 4/1969 | Van Mil, Jr. | 206/812 X |
| 3,608,566 | 9/1971 | Storandt | 206/484 X |
| 3,657,760 | 4/1972 | Kudisch | 206/484 X |
| 4,350,246 | 9/1982 | Mayer | 206/210 |
| 4,362,241 | 12/1982 | Williams | 206/219 X |
| 4,372,098 | 2/1982 | Mason | 53/412 |
| 4,427,111 | 1/1984 | Laipply | 206/441 X |
| 4,442,655 | 4/1984 | Stroetmann | 53/428 |
| 4,537,807 | 8/1985 | Chan et al. | 206/812 X |
| 4,678,698 | 7/1987 | Mencke | 206/812 X |
| 4,749,080 | 6/1988 | Toohey | 206/210 |

FOREIGN PATENT DOCUMENTS 788314 6/1968 Canada .......................... 206/484

Primary Examiner—Bryon Gerhman
Attorney, Agent, or Firm—Blum Kaplan

[57] ABSTRACT

A presaturated wipe product having a dilute glutaraldehyde saturated pad secured to a layer of packaging material is provided. The saturated pad is sealed in the packaging and the entire package is subjected to γ-irradiation in order to maintain the disinfectant activity of the pad over an extended period of time.

13 Claims, 3 Drawing Sheets

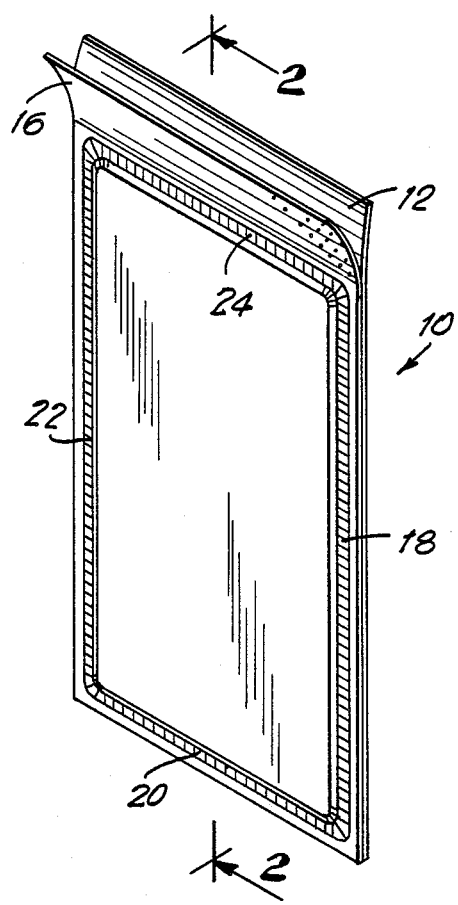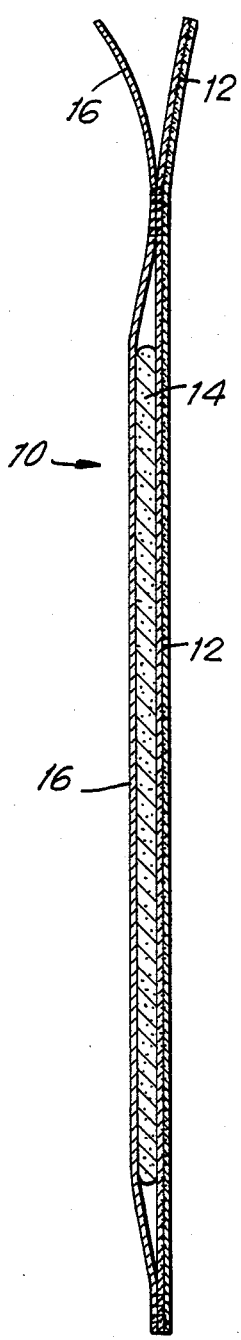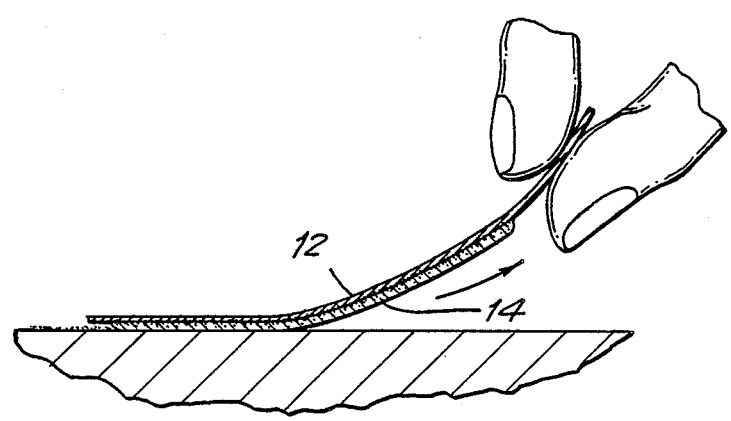
FIG. 1
FIG. 2
FIG. 6

ANTI-BACTERIAL AND ANTI-VIRAL PRESATURATED WIPE PRODUCT

BACKGROUND OF THE INVENTION

This invention relates to an anti-bacterial and anti-viral presaturated wipe product and to a method of manufacturing an antibacterial and anti-viral presaturated wipe product in a packaged form.

Disinfection of surfaces is an extremely important procedure in uncountable situations. For example, the surfaces of lab benches, animal cages, work stations, instruments and countertops in clinical as well as animal research laboratories must be disinfected on a regular basis. Other examples of surfaces requiring the use of disinfectants include, but are not limited to, medical applications such as table tops, beds, toilet facilities, bedpans, counters and doorhandles. Home, office and travel applications further include telephone receivers, shower stalls, kitchen counters and tools.

A disinfectant is an agent that disinfects by destroying, neutralizing or inhibiting the growth of harmful microorganisms. Not all disinfectants are effective against all types of bacterial and viral agents. Accordingly, a disinfectant can be contaminated by microorganisms that are resistant to the particular disinfectant.

In general, disinfectants are available in liquid form. The disinfectant is poured into a suitable container and diluted to the desired strength. Then a rag or other applicator is dipped into the disinfectant and used to apply the disinfectant to a surface. Alternatively, the disinfectant can be poured directly onto the surface and applied using a rag or other suitable applicator. These methods of disinfecting surfaces have numerous disadvantages.

Specifically, the rag or other applicator may contain a microorganism that will contaminate the disinfectant. In addition, the reason that it is necessary to dilute the disinfectant immediately prior to use is that diluted disinfectants generally become inactive within a short period of time. Concentrated disinfectants, in contrast, are unsafe for extended human or animal contact.

In the United States, it is the function of the Environmental Protection Agency (EPA) to approve disinfectants for specific uses. A disinfectant cannot be sold for use as a disinfectant in the United States without prior EPA approval.

In approving disinfectants, the EPA has a wide range of standards. If lesser standards are met, then lesser product claims can be made on the label of the disinfectant. As stricter standards are complied with, different product claims can be made.

The product claim of a hospital disinfectant is a particularly stringent product claim if made in compliance with EPA regulations. To date, no presaturated wipes have been approved by the EPA as a hospital disinfectant. In fact, it has been necessary for the EPA to modify their own test protocols in order to set the standards for a presaturated wipe in accordance with the invention.

Accordingly, it is desirable to provide a presaturated wipe and method of manufacturing the same that overcomes the disadvantages of known prior art disinfectant products.

SUMMARY OF THE INVENTION

Generally speaking, in accordance with the invention a presaturated wipe product and method of making such a presaturated wipe product is provided. The product comprises a glutaraldehyde saturated pad secured to a packaging material. The saturated pad is sealed in the packaging and the entire package is subjected to gamma irradiation. Accordingly, a presaturated wipe product that has been approved by the Environmental Protection Agency as a hospital disinfectant is provided.

It is, therefore, an object of the invention to provide a presaturated anti-bacterial and anti-viral wipe.

It is a further object of the invention to provide a presaturated wipe that uses a chemical that is sufficiently potent to kill specific bacteria and viruses and that is safe to the user.

It is a further object of the invention to provide a presaturated wipe product that is saturated with a disinfecting chemical in a diluted state and that has an extended shelf life.

It is yet another object of the invention to use a presaturated wipe product that uses a wiping material that does not interact with the disinfectant chemical.

It is still another object of the invention to minimize contamination of the wipe product after packaging.

It is still another object of the invention to provide a package that can be used as an applicator.

It is a further object of the invention to provide a product that qualifies as a hospital disinfectant in accordance with Environmental Protection Agency standard guidelines.

Still other objects and advantages of the invention will in part be obvious and will in part be apparent from the specification.

The invention accordingly comprises the article possessing the features, properties and the relation of elements and the several steps and the relation of one or more of such steps with respect to each of the others, which are exemplified in the following detailed disclosure, and the scope of the invention will be indicated in the claims.

DESCRIPTION OF THE DRAWINGS

For a fuller understanding of the invention, reference is had to the following description taken in connection with the accompanying drawings, in which:

FIG. 1 is a perspective view of a partially opened presaturated wipe product constructed and arranged in accordance with the invention;

FIG. 2 is a sectional view taken along line 2—2 of FIG. 1;

FIG. 6 is a sectional view taken along line 6—6 of FIG. 5; and

DETAILED DESCRIPTION OF THE INVENTION

Referring now to FIGS. 1 and 2, a presaturated wipe product, generally indicated as 10, constructed and arranged in accordance with a preferred embodiment of the invention is shown. Presaturated wipe product 10 comprises first layer 12 of packaging material, a second layer 16 of packaging material and a presaturated pad 14 secured to second layer 16.

Figure 7:
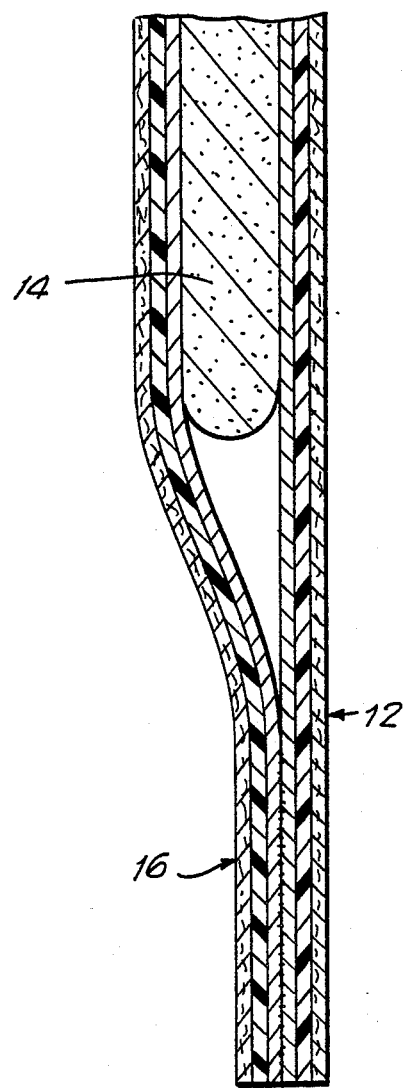
FIG. 7 is sectional view of a presaturated wipe product constructed and arranged in accordance with an alternate embodiment of the invention.

First and second layers 12 and 16, each include a layer of aluminum foil and a layer of polyethylene. Such layers 12 and 16 must be gas and liquid impermeable so as to create a barrier that prevents contaminants from entering the package once the package has been sealed. In addition, evaporation of the disinfectant used to saturate pad 14 through layers 12 and 16 also prevented. In an exemplary embodiment of the invention shown in FIG. 7, the packaging material is at least one layer of foil, at least one layer of polyethylene and, optionally, at least one layer of paper or one additional layer of foil. When used, the paper layer has a label or other useful information printed thereon. Such a multi-layer structure significantly reduces permeability of the packaging material to gasses. It is to be understood that the packaging material chosen is not limited to those materials specifically disclosed herein, but any packaging material that is capable of defining a layer that can provide a gas and liquid impermeable barrier can suitably be used.

Furthermore, pad 14 can be constructed of any suitable material, including, but not limited to, rayon, cotton, dacron and the like. The sole requirement is that the pad material must not be chemically reactive with the disinfectant solution that is to be impregnated therein. In an especially preferred embodiment, a nonwoven material is used. In general, nonwoven materials are capable of absorbing greater amounts of liquid than woven materials.

Pad 14 is glued to layer 16 using a suitable adhesive material such as glue. Pad 14 may be secured to layer 16 by glue over an entire surface of pad 14. Alternatively, pad 14 can be secured to second packaging material 16 using glue along only one edge or only at selected points. The precise means of securing pad 14 to second packaging material 16 is not considered to be a critical aspect of the invention and any bonding agent can be used.

The pad is saturated with a dilute solution comprising less than about 2% glutaraldehyde, preferably, 0.25% glutaraldehyde, 1.5% triethylene glycol, 0.75% inert ingredients and 97.5% water. Glutaraldehyde is generally sold in solutions of varying concentrations. For example, solutions of 10% glutaraldehyde, 60% triethylene glycol and 30% inert ingredients are commercially available. However, such concentrated glutaraldehyde solutions are not suitable for use directly as a disinfectant and must be diluted, specifically, at a ratio of about 40 parts water to 1 part glutaraldehyde solution. In an exemplary embodiment of the invention, distilled water is used to dilute the glutaraldehyde.

Pad 14 is saturated with the 0.25% glutaraldehyde solution. In an exemplary embodiment, five and eight-tenths (5.8) ml of 0.25% glutaraldehyde solution is used per 1.5"×2.875" area of pad 14. Proportionately larger amounts of liquid are used for larger sized pads.

Once pad 14 is saturated, first layer 12 is heat sealed to second layer 16 along each of edges 18, 20, 22 and 24. In an exemplary embodiment of the invention, the heat seal does not extend the entire distance to edge 24. This allows room for insertion of a finger or other object between first layer 12 and second layer 16 to permit easy separation of the layers to facilitate opening the presaturated wipe product.

Following heat sealing first layer 12 to second layer 16, the entire sealed package is subjected to gamma ($\gamma$) irradiation. Gamma irradiation prevents microbial growth inside the product and maintains the effectiveness of the dilute disinfectant over an extended period of time. The $\gamma$-irradiation can be applied at levels from about 0.05 to 2.0 megarads (mR). Most preferably, the amount of $\gamma$-irradiation is less than about 1.0 mR.

By following these procedures, a presaturated wipe product 10 that retains its disinfectant activity over an extended period of time is provided. The product is effective on a surface area up to 40 times larger than the size of presaturated pad 14. The following test results show the efficacy of a presaturated wipe product prepared in accordance with the invention.

Figure 3:
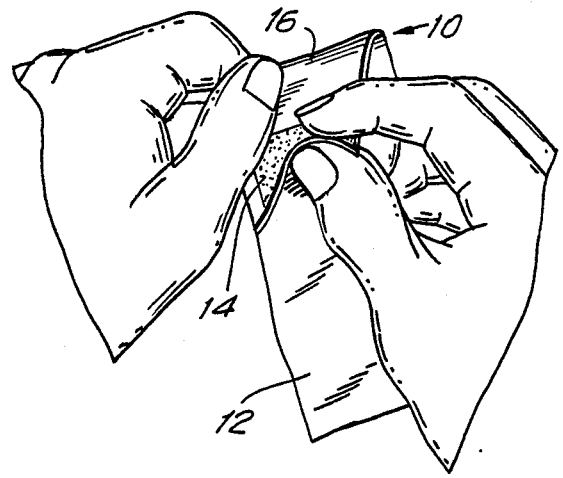
FIG. 3 is a perspective view of a presaturated wipe product constructed and arranged in accordance with the invention being opened by a user.
Figure 4:
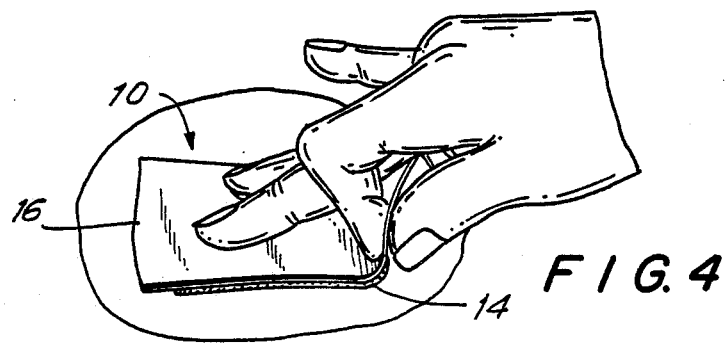
FIG. 4 is a perspective view of a presaturated wipe product of the invention in use.
Figure 5:
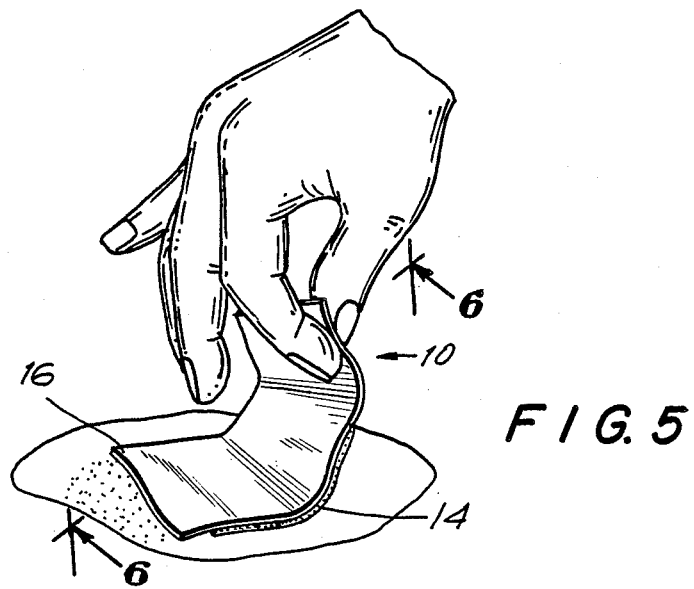
FIG. 5 is a perspective view of a presaturated wipe product of the invention shown after being used.

In order to determine the disinfecting activity of the presaturated wipe product constructed and arranged in accordance with the invention, presaturated wipe products 10 were opened and used as shown in FIGS. 3, 4 and 5 to wipe bacterially contaminated 1"×1" glass slides. After wiping, the slides were subcultured into a growth medium in order to determine whether viable organisms remained on the slides. Liquid expressed from the used wipe products was also subcultured.

Pseudomonas aeruginosa was used as a test organism. A 5% soil load was included in the test by adding 1 ml of horse serum to 19ml of innoculum. Sixty one inch square glass slides were inoculated with the test organism and were dried for 30 minutes at 37° C. Viable microbial concentrations on the untreated control carriers were determined as follows:

The slides were aseptically transferred to a 10 ml letheen dilution water blank/sea sand and sonicated for 15 seconds. The rinse solution from the slides was pooled and ten fold serial dilutions through $10^4$ of the contents of the 100 ml rinse system were prepared. One ml aliquots of appropriate dilutions were plated onto the slides using the Pour-plate Method and Standard Methods Agar (10–12ml/plate). All of the slides were incubated at 37° C. for 48 hours. Counts were conducted at the end of the incubation period with the aid of a Quebec Colony Counter. Counts on slides that had not been allowed to dry were obtained in the same manner.

To determine the average number of surviving organisms per cylinder, bacterial colonies were counted on plates yielding 30–300 colonies per plate. The counts on duplicate plates were averaged and the resulting average multiplied by the reciprocal of the respective dilution factor yielding the number of organisms per ml of the rinse blank. This value was multiplied by the volume of rinse solution (in ml) divided by the number of cylinders placed in the volume of rinse solution.

The results are shown in Table I.

TABLE I

| | SURVIVAL OF INOCULUM ON CONTAMINATED CARRIER | | | | |
|---|---|---|---|---|---|
| Test Date | Inoculum | Type of Carrier | Total Plate Count of Serial Dilutions of Rinse Solution | | Surviving Organisms Per Carrier |
| | | | $10^{-2}$ | $10^{-3}$ $10^{-4}$ | |
| 09/12/85 | Ps. aeruginosa | Wet | TNC* | TNC  197 | |
| | | | TNC | TNC  162 | $1.8 \times 10^7$ |
| | | Dry | TNC | 305  47 | |

TABLE I-continued

SURVIVAL OF INOCULUM ON CONTAMINATED CARRIER

| Test Date | Inoculum | Type of Carrier | Total Plate Count of Serial Dilutions of Rinse Solution $10^{-2}$ | $10^{-3}$ | $10^{-4}$ | Surviving Organisms Per Carrier |
|---|---|---|---|---|---|---|
| | | | TNC | <u>337</u> | 25 | $3.2 \times 10^6$ |

*TNC = Too Numerous to Count
Underlined values were used to calculate number of organisms Instead of spraying the surface of the dried inoculated glass slide, a single presaturated towelette was used for wiping the surface of three 1"×1" glass slides for a total use of 20 towelettes per 60 slides or carriers. The top, middle and bottom areas of the towelette were used to wipe. Each slide was wiped for 60 seconds and allowed to dry for 3 minutes. The dried slide was then transferred into 20ml of AOAC Letheen Broth. Secondary subcultures were made 30 minutes after the primary.

The used towelette was squeezed, allowing the excess liquid to drain into a sterile Petri dish. A 0.1 ml aliquot of the fluid expressed from the towelette was transferred into 9.9 ml of AOAC Letheen Broth. The used towelette was discarded.

The results are shown in Table II.

TABLE II

Test Organism: *Pseudomonas aeruginosa* PRD-10, ATCC No. 15442 plus 5% soil load

| Number of Wipes Used | Number of Carriers Treated Per wipe | Number of Carriers Showing Growth Over Number Tested | | Total Number of Positive Carriers |
|---|---|---|---|---|
| | | Primary | Secondary | |
| 20* | 3 | 1/60 | 0/60 | 1 |

*No growth was observed in the sub-culture media of 0.1 ml of liquid expressed from the 20 used wipes.

As can be seen from these results, the presaturated wipe product constructed and arranged in accordance with the invention was an effective disinfectant against pseudomanas aeruginosa. Similar tests were conducted and the presaturated wipe products of the invention were also found to be effective disinfectants against Salmonella cholorasis (a gram negative bacteria), Staphlococcus aureus (a gram positive bacteria), Proteus mirabilis, Serratia moroeses, Escheria coli, as well as against certain viral agents.

The product constructed and arranged in accordance with the invention has good efficacy against germs and is non-toxic to humans. In addition, by securing the pad to the packaging material, the product can be used without coming into contact with human skin. The product qualifies as a hospital disinfectant and has low odor and low residue. Accordingly, a presaturated wipe product that is safe, convenient, effective, economical and has good protocols is provided.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A presaturated wipe product for applying an active disinfectant solution to a work surface comprising:
   a first layer of packaging material;
   a second layer of packaging material;
   a pad secured to said second layer;
   a dilute glutaraldehyde solution impregnated in the pad for providing disinfecting activity to the pad;
   wherein the first layer and the second layer are heat sealed to each other so as to form a sealed envelope for maintaining the presaturated pad therein; and
   further wherein the presaturated pad has been γ-irradiated after the first and second layers are heat sealed so that said envelope maintains disinfecting activity for the glutaraldehyde over an extended period of time.

2. The presaturated wipe product of claim 1, wherein at least one of the layers of packaging material comprises a layer of foil and a layer of polyethylene.

3. The presaturated wipe product of claim 2, wherein the at least one layer comprising a layer of foil and a layer of polyethylene further comprises a layer of paper.

4. The presaturated wipe product of claim 1, wherein the pad is secured to the second layer using a bonding adhesive.

5. The presaturated wipe product of claim 1, wherein the pad is a nonwoven material.

6. The presaturated wipe product of claim 5, wherein the nonwoven material is rayon.

7. The presaturated wipe product of claim 1, wherein the dilute glutaraldehyde solution comprises less than about 2% glutaraldehyde.

8. The presaturated wipe product of claim 7, wherein the dilute glutaraldehyde solution comprises about 0.25% glutaraldehyde, about 1.5% triethylene glycol, about 0.75% inert ingredients and about 97.5% water.

9. The presaturated wipe product of claim 8, wherein the water used to prepare the dilute glutaraldehyde solution is distilled water.

10. The presaturated wipe product of claim 1, wherein the presaturated wipe product is effective on a surface having a surface area up to 40 times greater than the area of the presaturated pad.

11. The presaturated wipe product of claim 1, wherein the product is effective against gram negative bacteria, gram positive bacteria and viral agents.

12. A presaturated wipe for applying an active disinfectant solution to a work surface prepared by the process comprising:
   securing a pad to a first layer of packaging material;
   impregnating said pad with a dilute glutaraldehyde solution for providing disinfecting activity to the pad;
   heat sealing the first layer to a second layer of packaging material to form a sealed envelope for maintaining the presaturated pad therein; and
   subjecting the sealed enveloped to γ-irradiation in order to prevent microbial growth inside the envelope and to maintain the effectiveness of the dilute glutaraldehyde solution over an extended period of time.

13. The product prepared by the process of claim 12, wherein the γ-irradiation is used at an intensity of less than about 1.0 mR.

* * * * *